(12) United States Patent
Lee et al.

(10) Patent No.: US 8,124,762 B2
(45) Date of Patent: Feb. 28, 2012

(54) DIPHENYL AMINE DERIVATIVES HAVING LUMINESCENCE PROPERTY

(75) Inventors: So Ha Lee, Seoul (KR); Jae Chun Ryu, Seoul (KR); Kyung Ho Yoo, Seoul (KR); Ibrahim Mustafa El-Deeb, Seoul (KR)

(73) Assignee: Korea Institute of Science & Technology, Seoul (KR)

( * ) Notice: Subject to any disclaimer, the term of this patent is extended or adjusted under 35 U.S.C. 154(b) by 657 days.

(21) Appl. No.: 12/329,523

(22) Filed: Dec. 5, 2008

(65) Prior Publication Data

US 2010/0063281 A1    Mar. 11, 2010

(30) Foreign Application Priority Data

Sep. 5, 2008   (KR) ......................... 10-2008-0087808
Nov. 5, 2008   (KR) ......................... 10-2008-0109444

(51) Int. Cl.
*C07D 239/02* (2006.01)
*C09K 11/06* (2006.01)

(52) U.S. Cl. ............... 544/322; 252/301.16; 252/301.26
(58) Field of Classification Search .................. 544/322; 252/301.16, 301.26
See application file for complete search history.

(56) References Cited

FOREIGN PATENT DOCUMENTS

WO       2010/024572     *   3/2010

OTHER PUBLICATIONS

Wu, Fang-Iy et al.: "Bis(2,2-diphenylvinyl)spirobifluorene: An efficient and stable blue emitter for electroluminescence applications", *Synthetic Metals*, 151 (2005) pp. 285-292.
Pope, Martin et al.: "Double-Quantum External Photoelectric Effect in Organic Crystals", *The Journal of Chemical Physics*, vol. 42, No. 7, Apr. 1, 1965, pp. 2540-2543.
Helfrich, W. et al.: "Recombination Radiation in Anthracene Crystals", *Physical Review Letters*, vol. 4, No. 7, Feb. 15, 1965, pp. 229-231.
Tang, C.W. et al.: "Electroluminescence of doped organic thin films", *J.Appl.Phys.*, 65(9), May 1, 1989, pp. 3610-3616.

* cited by examiner

*Primary Examiner* — James O Wilson
*Assistant Examiner* — Ebenezer O Sackey
(74) *Attorney, Agent, or Firm* — Frommer Lawrence & Haug LLP; Ronald R Santucci

(57) ABSTRACT

The present invention relates to diphenyl amine derivatives having luminescent properties, and particularly to diphenyl amines substituted with various electron-donating or electron-withdrawing groups. The compounds of the present invention show blue or blue-green luminescence, and luminescence of the compounds herein can be achieved by UV or visible light, thus being useful as a fluorescent dye or fluorescent material for an organic electroluminescence device or display.

4 Claims, No Drawings

DIPHENYL AMINE DERIVATIVES HAVING LUMINESCENCE PROPERTY

CROSS-REFERENCE TO RELATED APPLICATION

This application claims under 35 U.S.C. §119(a) the benefit of Korean Patent Application Nos. 10-2008-0087808 filed Sep. 5, 2008, and 10-2008-0109444 filed Nov. 5, 2008, the entire contents of which are incorporated herein by reference.

BACKGROUND (a) Technical Field

The present invention relates to diphenyl amine derivatives having luminescence property, and particularly to diphenyl amines substituted with various electron-donating or electron-withdrawing groups. The compounds of the present invention show blue or blue-green luminescence, and luminescence of the compounds herein can be achieved by UV or visible light, thus being useful as a fluorescent material or an organic electroluminescence device or display.

(b) Background Art

Electroluminescence, referred to as "EL" hereinafter, of organic materials was achieved by using anthracene single crystals in 1965 by W. Helfrich (W. Helfrich and W. G. Schreider, *Phys. Rev. Lett.*, 1965. 14, 229) and M. Pope (M. Pope, H. Kallmann, *J. Chem. Phys.*, 1965, 42, 2540) et al. However, little attention was drawn to this because luminescence efficiency was too low and a relatively high voltage was required. Since Tang (C. W. Tang, S. A. VanSlyke and C. H. Chen., *J. Appl. Phys.*, 1989, 65, 3610) developed organic EL devices operable at a relatively low voltage and showing a high brightness in 1986, extensive researches have been exerted worldwide. Recently commercialized organic EL devices can be operated at a relatively low voltage and show a wide viewing angle and a prompt response.

To obtain an organic EL display with superior properties, the development of luminescence materials showing various colors such as blue, blue-green, red and orange is necessary. Tris(8-hydroxyquinoline)aluminum ('Alq$_3$') is known as green luminescence material, which was developed in 1987 by Kodak. Other compounds such as quinacridone, coumarin derivatives, DPT and BDAC have also been developed. N,N'-bis(3-methylphenyl)-(1,1'-biphenyl)-4,4'-diamine ('DPVBi') and Alq$_3$ have been developed as a blue luminescence. DCM$_2$ and DCTTB have been developed by Kodak as a red luminescence material. Besides, rubrene and BTX have been developed as yellow and orange luminescence materials, respectively. The conventional red and blue luminescence materials are known to be problematic in luminescence yield and durability, respectively.

SUMMARY OF THE DISCLOSURE

The present inventors have exerted extensive researches to overcome the aforementioned problems, and have finally developed a novel luminescent material that shows blue or blue-green luminescence by UV or visible light, thereby completing the present invention.

In one aspect, the present invention relates to diphenyl amine derivatives of a novel structure.

In another aspect, the present invention relates to a process of preparing the novel diphenyl amine derivatives.

In still another aspect, the present invention relates to the use of the novel diphenyl amine derivatives as a blue or blue-green fluorescent dye or fluorescent substance.

In a further aspect, the present invention relates to the use of the novel diphenyl amine derivatives as fluorescent substance for electronic materials such as an organic electroluminescence device or display.

The present invention provides diphenyl amine derivatives of Formula 1 that show luminescence by UV or visible light, thereby enabling to overcome the aforementioned problems.

Formula 1

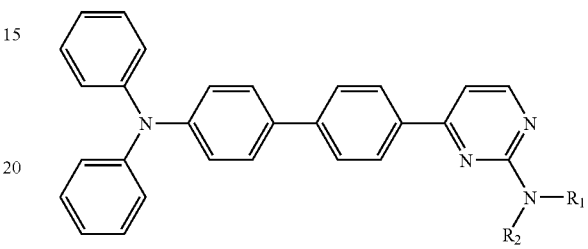

In the above Formula 1, each of $R_1$ and $R_2$ is selected from the group consisting of a hydrogen atom; a $C_1$-$C_8$ alkyl; a substituted or unsubstituted phenyl; a biphenyl; a substituted or unsubstituted naphthyl; and substituted or unsubstituted benzyl groups, wherein the substituted benzyl group is substituted with a $C_1$-$C_8$ alkyl or a $C_1$-$C_8$ alkoxy group; and each of the substituted phenyl and the substituted naphthyl groups are substituted with 1-3 substituent(s) selected from the group consisting of a halogen atom, cyano, nitro, carboxyl, sulfonyl, hydroxy, amino, a $C_1$-$C_8$ alkylamino, a $C_1$-$C_8$ alkyl, a $C_1$-$C_8$ alkoxy, a $C_2$-$C_8$ alkenyl, phenyl, 4-styryl, phenoxy, naphthoxy, phenylamino, and naphthylamino groups.

DETAILED DESCRIPTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

Diphenyl amine derivatives of Formula 1 according to the present invention show blue or blue-green luminescence. Further, luminescence of the compounds herein can be achieved by UV or visible light. Therefore, the present invention discloses diphenyl amine derivatives of Formula 1 as blue or blue-green fluorescent dye or fluorescent substance, and also discloses the use of diphenyl amine derivatives of Formula 1 as electronic material such as organic electroluminescence (EL) device or display.

In a preferred embodiment, the present invention relates to diphenyl amine derivatives of Formula 1, wherein each of $R_1$ and $R_2$ is selected from the group consisting of a hydrogen atom; an alkyl selected from the group consisting of methyl, ethyl, n-propyl, isopropyl, n-butyl, sec-butyl and tert-butyl groups; phenyl; biphenyl; naphthyl; and a substituted or unsubstituted benzyl group; and the substituted benzyl group is substituted with substituent(s) selected from the group consisting of methyl, ethyl, n-propyl, isopropyl, n-butyl, sec-butyl, tert-butyl, methoxy, ethoxy, n-propoxy, isopropoxy, n-butoxy, sec-butoxy, and tert-butoxy groups.

Examples of the diphenyl amine derivatives of Formula 1 herein include, but are not limited to:

1-(4'-diphenylaminobiphenyl-4-yl)ethanone,
1-(4'-diphenylaminobiphenyl-4-yl)-3-dimethylaminoprop-2-en-1-one,
4-(4'-diphenylaminobiphenyl-4-yl)pyrimidine-2-amine,
[4-(4'-diphenylaminobiphenyl-4-yl)pyrimidine-2-yl]dibenzylamine,
[4-(4'-diphenylaminobiphenyl-4-yl)pyrimidine-2-yl]bis(4-methoxybenzyl)amine,
[4-(4'-diphenylaminobiphenyl-4-yl)pyrimidine-2-yl]bis(4-methylbenzyl)amine,
[4-(4'-diphenylaminobiphenyl-4-yl)pyrimidine-2-yl]dimethylamine,
[4'-[2-(1,3-dihydroindole-2-yl)pyrimidine-4-yl]biphenyl-4-yl]diphenyl amine,
[4-(4'-diphenylaminobiphenyl-4-yl)pyrimidine-2-yl]phenylamine,
[4-(4'-diphenylaminobiphenyl-4-yl)pyrimidine-2-yl]naphthalene-2-ylamine,
[4-(4'-diphenylaminobiphenyl-4-yl)pyrimidine-2-yl]biphenyl-4-ylamine,
[4-(4'-diphenylaminobiphenyl-4-yl)pyrimidine-2-yl]methyl phenylamine,
[4-(4'-diphenylaminobiphenyl-4-yl)pyrimidine-2-yl]methyl naphthalene-2-ylamine, and
[4-(4'-diphenylaminobiphenyl-4-yl)pyrimidine-2-yl]methyl biphenyl-4-ylamine.

The aforelisted compounds have the following structures, respectively.

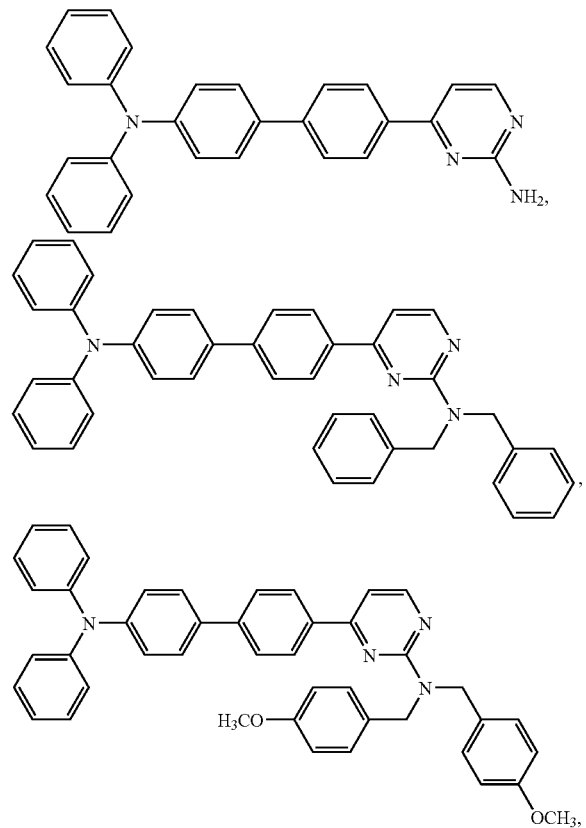

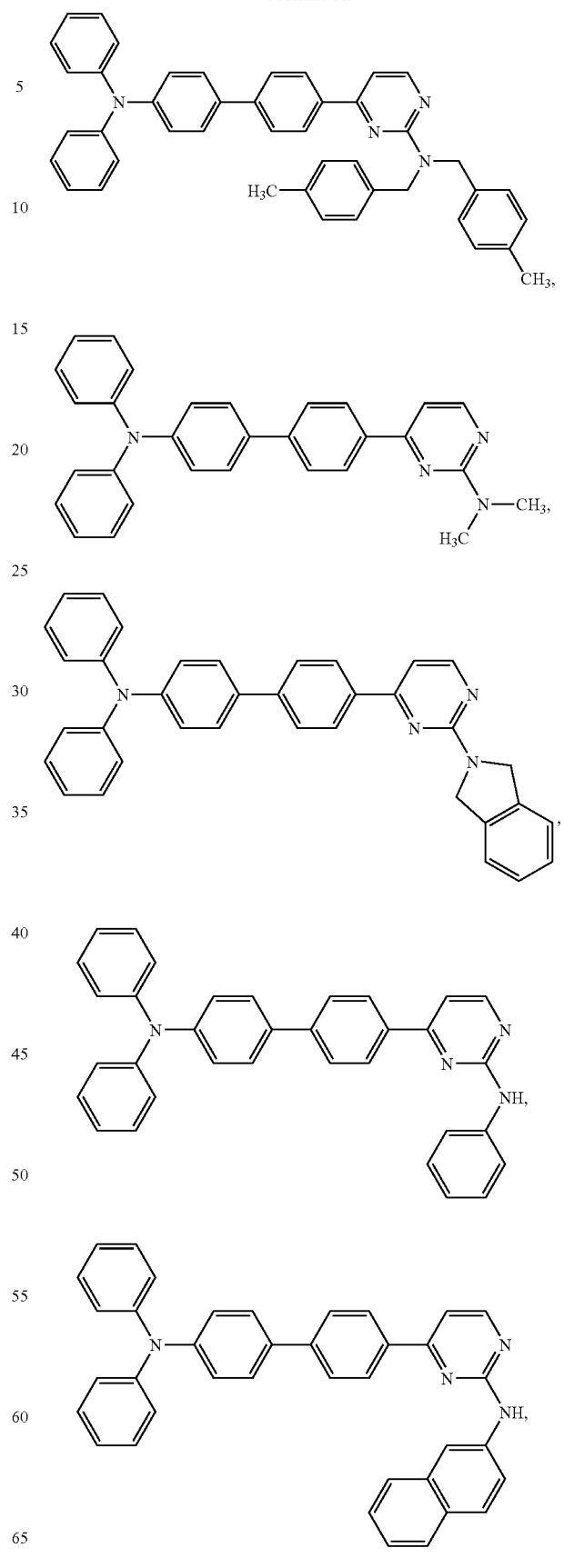

-continued

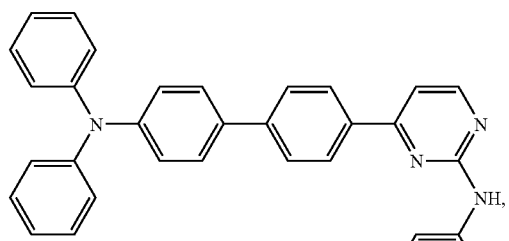

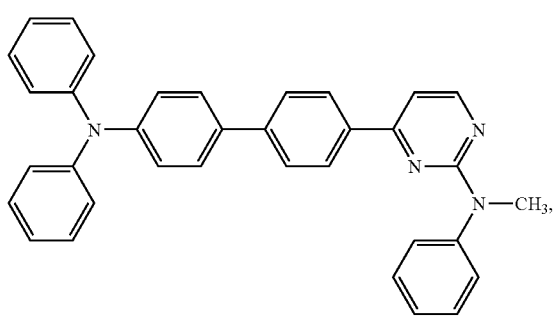

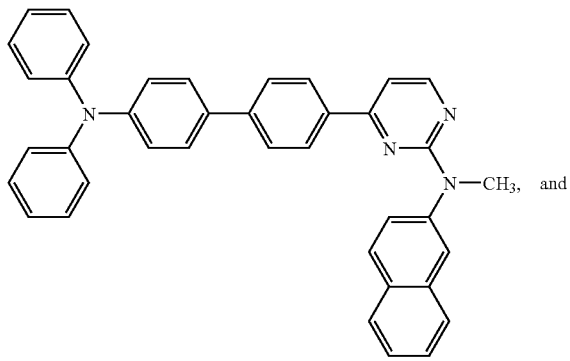

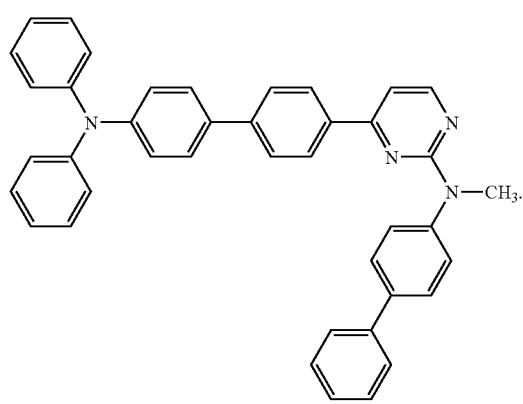

The present invention also discloses a process of preparing diphenyl amine derivatives (phenyldiamine derivatives?) of Formula 1. A process herein comprises the following steps:

(a) preparing an ethanone compound of Formula 4 by reacting a bromide compound of Formula 2 with a borate compound of Formula 3 in the presence of palladium(Pd) catalyst and under nitrogen atmosphere;

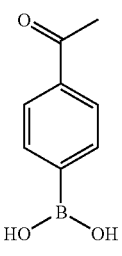

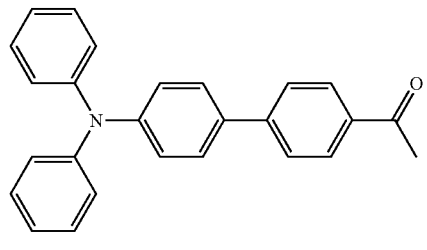

(b) preparing a propenone compound of Formula 5 by reacting the ethanone compound of Formula 4 with N,N-dimethylformamide dimethylacetal;

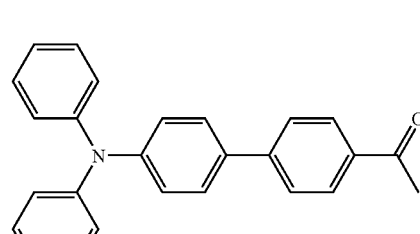

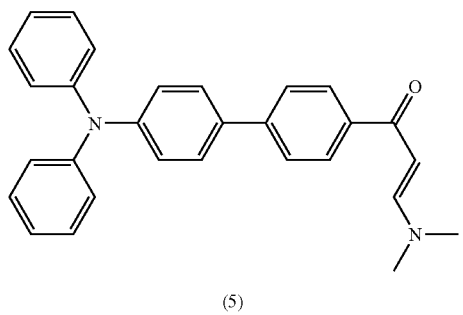

(5)

(c) preparing an amine compound of Formula 1a by reacting the propenone compound of Formula 5 with sodium ethoxide and guanidine hydrochloride; and

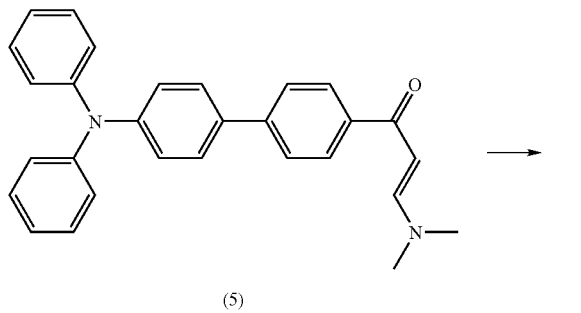

(d) preparing the diphenyl amine derivatives of Formula 1 by reacting the amine compound of Formula 1a with a halide compound of R₁—X or R₂—X;

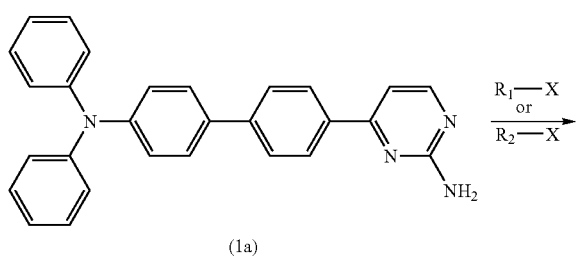

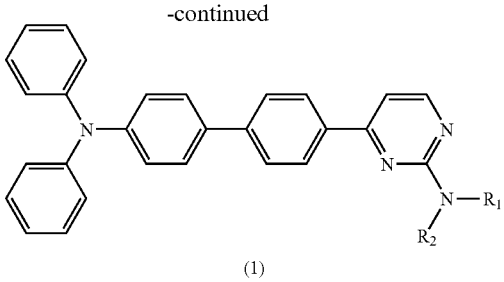

(1)

wherein X is a halogen atom; each of $R_1$ and $R_2$ is same as defined in claim 1.

Hereunder is provided a detailed description of a process herein. The step (a) is conducted to prepare the ethanone compound of Formula 4 by reacting the bromide compound of Formula 2 with the borate compound of Formula 3.

This reaction is conducted by using the conventional solvent under nitrogen atmosphere in the presence of palladium (II) catalyst and a base. Examples of a solvent include, but are not limited to, haloalkanes such as chloroform and dichloromethane; nitrites such as acetonitrile; sulfoxides such as dimethylsulfoxide (DMSO); ethers such as diethylether; amides such as dimethylformamide (DMF); alcohols such as methanol; water; and a mixture thereof. A mixture of acetonitrile and water is preferred. Example of palladium catalyst include, but are not limited to, dichlorobis(triphenylphosphine)palladium(II). Examples of a base include, but are not limited to, inorganic or organic base such as carbonate of alkali or alkaline earth metal. The step (a) can be conducted at 10-30° C. Reaction can be completed at atmospheric temperature after 3-6 hours although reflux can be conducted, if necessary.

The step (b) is conducted to prepare the propenone compound of Formula 5 by reacting the ethanone compound of Formula 4 with N,N-dimethylformamide dimethylacetal. N,N-dimethylformamide dimethylacetal is preferred to be used in the amount of 2-5 equivalents with reference to the ethanone compound of Formula 4. The reaction can be completed at 60-150° C. after 10-15 hours.

The step (c) is conducted to prepare the amine compound of Formula 1a by reacting the propenone compound of Formula 5 with sodium ethoxide and guanidine hydrochloride. Sodium ethoxide used in the reaction is prepared by dissolving sodium (Na) in anhydrous ethanol. The reaction can be conducted at 60-200° C., preferably at reflux temperature. The reaction can be completed after 10-15 hours at the aforementioned temperature.

The step (d) is conducted to prepare the diphenyl amine derivatives of Formula 1 by reacting the amine compound of Formula 1a with various halide compounds of $R_1$—X or $R_2$—X. The substitution reaction is conducted by using halide compound of $R_1$—X or $R_2$—X at atmospheric temperature or a reflux temperature, specifically at 20-150° C. An appropriate base can be selected, and examples of such bases include, but are not limited to, hydride of alkali metals and halide or hydroxide or carbonate of alkali or alkaline earth metals.

Representative substitution reactions are shown in Scheme 2 depending on the kind of halide compound.

Scheme 2
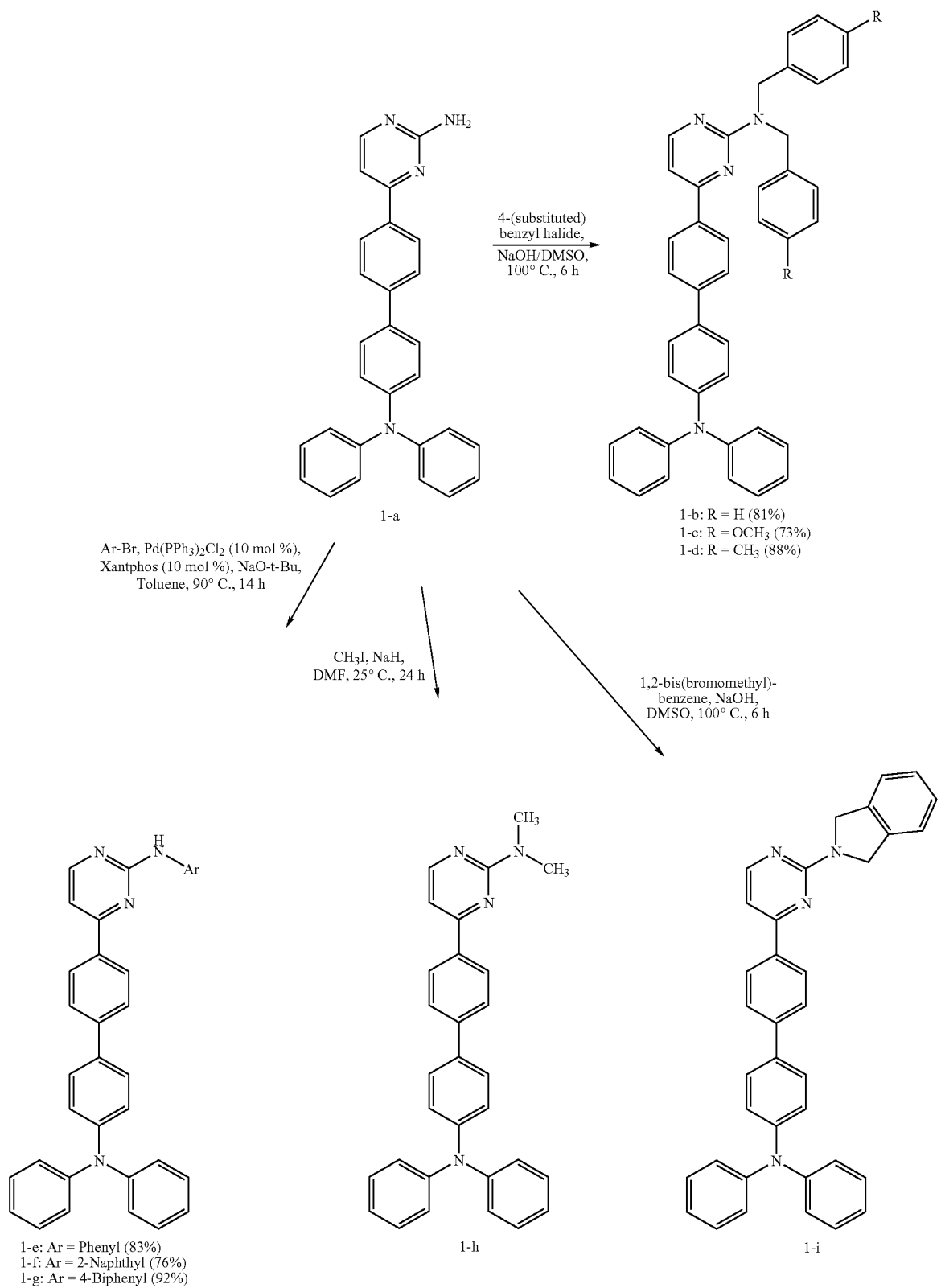

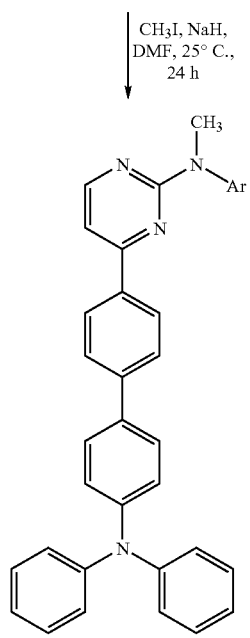

1-j: Ar = Phenyl (31%)
1-k: Ar = 2-Naphthyl (46%)
1-l: Ar = 4-Biphenyl (59%)

Hereunder is provided a detailed description of the substitution reaction as shown in Scheme 2.

For example, compounds of Formulas 1-b, 1-c and 1-d can be prepared by reacting compounds of Formula 1-a with various kinds of substituted benzyl halides in dimethylsulfoxide (DMSO) in the presence of sodium hydroxide at 100° C. for 6-12 hours. Further, compounds of Formula 1-i can be prepared by reacting compounds of Formula 1-a with 1,2-bis(bromomethyl)benzene in dimethylsulfoxide (DMSO) in the presence of sodium hydroxide at 100° C. for 6-12 hours.

Compounds of Formula 1-h can be prepared by reacting compounds of Formula 1-a with methyl iodide ($CH_3I$) in dimethylformamide (DMF) in the presence of sodium hydride (NaH) at room temperature (20-30° C.) for 6-14 hours.

Compounds of Formulas 1-e, 1-f and 1-g can be prepared by reacting compounds of Formula 1-a in toluene in the presence of $Pd(PPh_3)_2Cl_2$, Xantphos and NaO-t-Bu at 90° C. for 6-14 hours. Then, corresponding compounds of Formulas 1-j, 1-k and 1-l can be prepared by reacting compounds of Formulas 1-e, 1-f and 1-g in dimethylformamide in the presence of sodium hydride (NaH) and methyl iodide ($CH_3I$) at room temperature (20-30° C.) for 24 hours.

As described above, diphenyl amine derivatives of Formula 1 can be prepared in high purity and yield according to a process of the present invention.

EXAMPLES

The following examples illustrate the invention and are not intended to limit the same.

Example 1

Preparation of 1-(4'-diphenylaminobiphenyl-4-yl)ethanone (Formula 4)

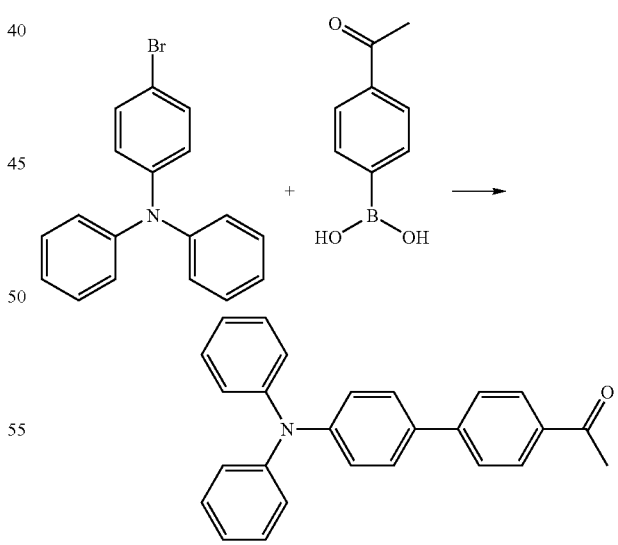

4-Bromotriphenylamine (2.0 g, 6.17 mmol), 4-acetylphenylboronic acid (1.12 g, 6.8 mmol), dichlorobis(triphenylphosphine)palladium(II) (130 mg, 0.185 mmol) and sodium carbonate (460 mg, 4.32 mmol) were added into a solvent mixture of acetonitrile and water (1:1, v/v, 80 mL), and heated under nitrogen at 80° C. for 3 hours. After the completion of the reaction, the reaction mixture was cooled to room temperature and added with water (80 mL), followed by the separation of the organic layer with dichloromethane (150 mL×3). The organic layer was filtered, dried and evaporated, and the resulting organic residue was purified by column chromatogram (silica gel, hexane: EtOAc=4:1) to obtain the title compound (1.7 g).

Yield 76%; mp 97-98° C.; FTIR (KBr, v/cm$^{-1}$) 1679, 1590, 1489, 1268, 821, 750, 697; $^1$H-NMR (300 MHz, CDCl$_3$, ppm) δ 2.65 (s, 3H), 7.08-7.30 (m, 12H), 7.53 (d, J=7.9 Hz, 2H), 7.67 (d, J=7.7 Hz, 2H), 8.03 (d, J=7.7 Hz, 2H); $^{13}$C-NMR (75 MHz, CDCl$_3$, ppm) δ 26.64, 123.29, 123.37, 124.79, 126.50, 127.29, 127.93, 128.98, 129.39, 133.13, 135.33, 145.21, 147.42, 148.19, 197.68; UV λ$_{max}$=365 nm (CH$_2$Cl$_2$); PL λ$_{max}$=500 nm (CH$_2$C$_2$).

Example 2

Preparation of 1-(4'-diphenylaminobiphenyl-4-yl)-3-dimethylaminoprop-2-en-1-one (Formula 5)

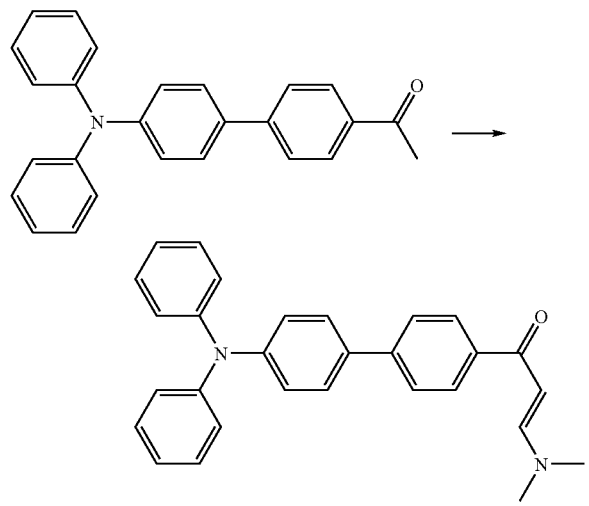

1-(4'-Diphenylaminobiphenyl-4-yl)ethanone (1.0 g, 2.75 mmol) was reacted with N,N-dimethylformamide dimethylacetal (1.0 g, 8.25 mmol) for 12 hours at 100° C. Non-reacted N,N-dimethylformamide dimethylacetal was removed using a vacuum pump, and water (50 mL) and dichloromethane (100 mL×2) added. The organic layer was separated, filtered, dried and evaporated to obtain the title compound (1.1 g).

Yield 97%; mp 166-167° C.; FTIR (KBr, v/cm$^{-1}$) 1677, 1642, 1591, 1576, 1488, 1273, 1243, 754, 695; $^1$H-NMR (300 MHz, CDCl$_3$, ppm) δ 2.99 (s, 3H), 3.13 (s, 3H), 5.79 (d, J=12.3 Hz, 1H), 7.06 (t, J=7.2 Hz, 2H), 7.15 (d, J=8.3 Hz, 6H), 7.26-7.32 (m, 4H), 7.52 (d, J=8.6 Hz, 2H), 7.63 (d, J=8.3 Hz, 2H), 7.84 (d, J=12.3 Hz, 1H), 7.98 (d, J=8.3 Hz, 2H); $^{13}$C-NMR (75 MHz, CDCl$_3$, ppm) δ 91.87, 92.21, 123.12, 123.62, 124.59, 126.22, 127.84, 128.12, 129.32, 134.13, 138.74, 143.08, 147.58, 147.66, 154.16, 188.08; UV λ$_{max}$=363 nm (CH$_2$Cl$_2$) PL λ$_{max}$=493 nm (CH$_2$Cl$_2$).

Example 3

Preparation of 4-(4'-diphenylaminobiphenyl-4-yl) pyrimidine-2-amine (compound 1-a)

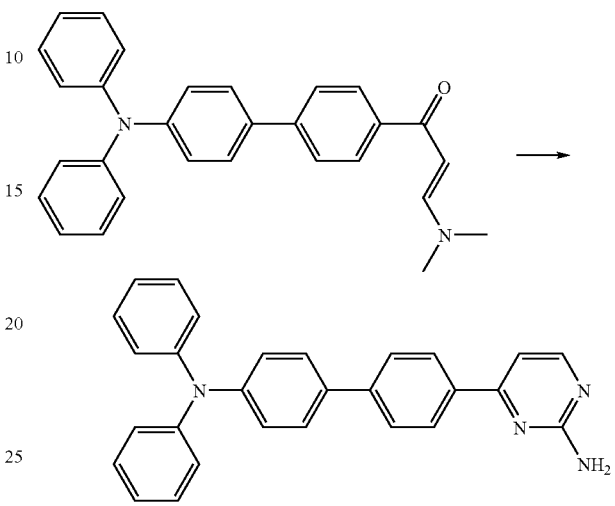

Sodium ethoxide was prepared by adding sodium (60 mg, 2.63 mmol) into anhydrous ethanol (20 mL), followed by slow addition of guanidine hydrochloride (250 mg, 2.63 mmol) for 1 hour at room temperature. This solution was added with a solution of (4'-diphenylaminobiphenyl-4-yl)-3-dimethylaminoprop-2-en-1-one (1.0 g, 2.39 mmol) in anhydrous ethanol (30 mL), and then refluxed for 12 hours and cooled to room temperature. Precipitated crystals were filtered, washed with cold ethanol and water, and filtered to obtain the title compound in crystalline form.

Yield 84%; mp 219-220° C.; FTIR (KBr, v/cm$^{-1}$) 3483, 3278, 1626, 1589, 1571, 1491, 1459, 1294, 810, 750, 698; $^1$H-NMR (300 MHz, CDCl$_3$, ppm) δ 6.67 (s, 2H), 7.03-7.11 (m, 8H), 7.16 (d, J=5.2 Hz, 1H), 7.31-7.36 (m, 4H), 7.67 (d, J=8.6 Hz, 2H), 7.76 (d, J=8.3 Hz, 2H), 8.13 (d, J=8.3 Hz, 2H), 8.30 (d, J=5.2 Hz, 1H); $^{13}$C-NMR (75 MHz, CDCl$_3$, ppm) δ 107.55, 123.18, 123.59, 124.63, 126.82, 127.51, 127.77, 129.34, 133.81, 135.39, 142.89, 147.55, 147.78, 158.57, 163.23, 165.08; UV λ$_{max}$=366 nm (CH$_2$Cl$_2$) PL λ$_{max}$=497 nm (CH$_2$Cl$_2$).

Example 4

Preparation of [4-(4'-diphenylaminobiphenyl-4-yl) pyrimidine-2-yl]dibenzylamine (compound 1-b)

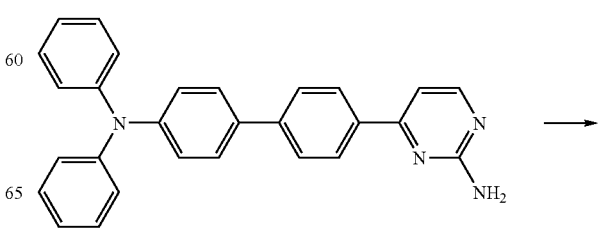

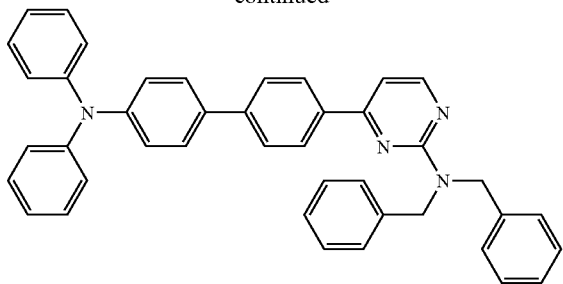

4-(4'-Diphenylaminobiphenyl-4-yl)pyrimidine-2-amine (100 mg, 0.24 mmol) and sodium hydroxide (38 mg, 0.96 mmol) were added in dimethylsulfoxide (1 mL), and mixed at 100° C. for 30 minutes. This solution was added with a solution of benzyl bromide (63.1 μL, 0.53 mmol) in dimethylsulfoxide (1 mL) at 100° C. for 30 minutes, followed by stirring for 5 hours. This solution was cooled and added with water (100 mL) and a saturated saline solution, and then allowed to stand for 24 hours. The precipitated crystalline material was purified by column chromatogram (silica gel, hexane: EtOAc=8:1) to give the title compound.

Yield 81%; mp 164-165° C.; FTIR (KBr, v/cm$^{-1}$) 1582, 1553, 1489, 1349, 1284, 805, 758, 699; $^1$H-NMR (300 MHz, CDCl$_3$, ppm) δ 5.01 (s, 4H), 7.04-7.09 (m, 3H), 7.16 (d, J=8.1 Hz, 5H), 7.27-7.33 (m, 15H), 7.52 (d, J=8.5 Hz, 2H), 7.66 (d, J=8.3 Hz, 2H), 8.12 (d, J=8.3 Hz, 2H), 8.44 (d, J=5.2 Hz, 1H); $^{13}$C-NMR (75 MHz, CDCl$_3$, ppm) δ 49.21, 105.57, 123.16, 123.60, 124.63, 126.72, 127.04, 127.51, 127.74, 128.51, 129.34, 133.95, 135.86, 138.60, 142.74, 147.57, 147.71, 158.30, 162.32, 164.05; UV λ$_{max}$=365 nm (CH$_2$Cl$_2$); PL λ$_{max}$=483 nm (CH$_2$Cl$_2$).

Example 5

Preparation of [4-(4'-diphenylaminobiphenyl-4-yl) pyrimidine-2-yl]bis(4-methoxy benzyl)amine (compound 1-c)

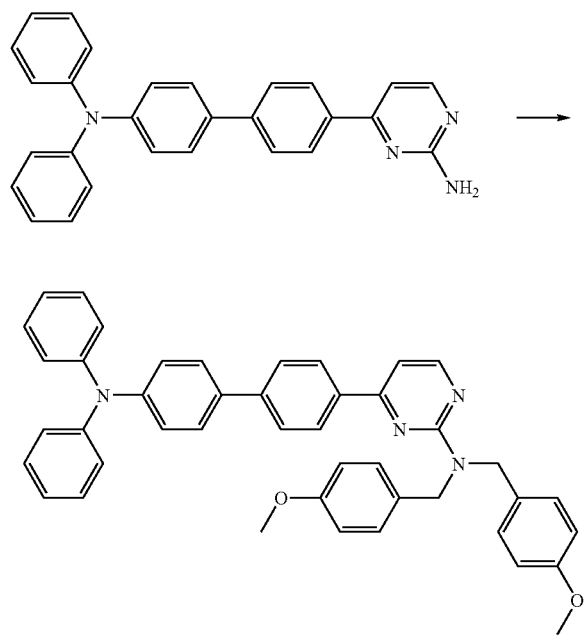

4-(4'-Diphenylaminobiphenyl-4-yl)pyrimidine-2-amine (100 mg, 0.24 mmol) and sodium hydroxide (38 mg, 0.96 mmol) were added in dimethylsulfoxide (1 mL), and stirred at 100° C. for 30 minutes. This solution was added with a solution of 4-methoxybenzyl bromide (74.2 μL, 0.53 mmol) in dimethylsulfoxide (1 mL) for 30 minutes at 100° C., followed by stirring for 5 hours. This solution was cooled and added with water (100 mL) and a saturated saline solution, and then allowed to stand for 24 hours. The precipitated crystalline material was purified by column chromatogram (silica gel, hexane:EtOAc=8:1) was purified to give the title compound.

Yield 73%; mp 95-97° C.; FTIR (KBr, v/cm$^{-1}$) 1585, 1558, 1509, 1490, 1347, 1282, 1244, 1172, 1033, 805, 754, 697; $^1$H-NMR (300 MHz, CDCl$_3$, ppm) δ 3.81 (s, 6H), 4.91 (s, 4H), 6.87 (d, J=8.4 Hz, 4H), 7.04-7.09 (m, 3H), 7.16 (d, J=8.1 Hz, 5H), 7.25-7.32 (m, 9H), 7.53 (d, J=9.0 Hz, 2H), 7.67 (d, J=8.2 Hz, 2H), 8.14 (d, J=8.2 Hz, 2H), 8.44 (d, J=5.1 Hz, 1H); $^{13}$C-NMR (75 MHz, CDCl$_3$, ppm) δ 48.20, 55.28, 105.37, 113.90, 123.14, 123.60, 124.62, 126.71, 127.47, 127.73, 129.05, 129.33, 133.98, 135.96, 142.68, 147.57, 147.69, 158.75 HRMS (C$_{44}$H$_{38}$N$_4$O$_2$) UV λ$_{max}$=363 nm (CH$_2$Cl$_2$); PL λ$_{max}$=479 nm (CH$_2$Cl$_2$).

Example 6

Preparation of [4-(4'-diphenylaminobiphenyl-4-yl) pyrimidine-2-yl]bis(4-methyl benzyl)amine (compound 1-d)

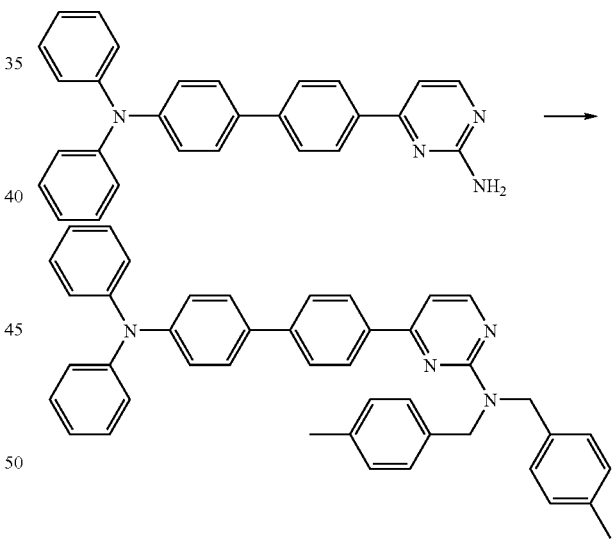

4-(4'-Diphenylaminobiphenyl-4-yl)pyrimidine-2-amine (100 mg, 0.24 mmol) and sodium hydroxide (38 mg, 0.96 mmol) were added in dimethylsulfoxide (1 mL), and stirred at 100° C. for 30 minutes. This solution was added with a solution of 4-methylbenzyl bromide (71.6 μL, 0.53 mmol) in dimethylsulfoxide (1 mL) at 100° C. for 30 minutes, and stirred for 5 hours. This solution was cooled and added with water (100 mL) and a saturated saline solution, and allowed to stand for 24 hours. The precipitated crystalline material was purified by column chromatogram (silica gel, hexane: EtOAc=8:1) to obtain the title compound (131 mg).

Yield 88%; mp 153-154° C.; FTIR (KBr, v/cm$^{-1}$) 1584, 1559, 1494, 1345, 1281, 798, 750, 697; $^1$H-NMR (300 MHz, CDCl$_3$, ppm) δ 2.35 (s, 6H), 4.95 (s, 4H), 7.04-7.32 (m, 21H), 7.53 (d, J=8.4 Hz, 2H), 7.65 (d, J=8.1 Hz, 2H), 8.12 (d, J=8.1 Hz, 2H), 8.43 (d, J=4.9 Hz, 1H); $^{13}$C-NMR (75 MHz, CDCl$_3$, ppm) δ 21.13, 48.66, 105.39, 123.14, 123.63, 124.62, 126.70, 127.48, 127.74, 129.17, 129.34, 134.03, 135.58, 136.02, 136.56, 142.62, 147.58, 147.67, 158.50, 162.50, 163.84; UV λ$_{max}$=365 nm (CH$_2$Cl$_2$); PL λ$_{max}$=479 nm (CH$_2$Cl$_2$).

Example 7

Preparation of [4-(4'-diphenylaminobiphenyl-4-yl)pyrimidine-2-yl]dimethylamine (compound 1-h)

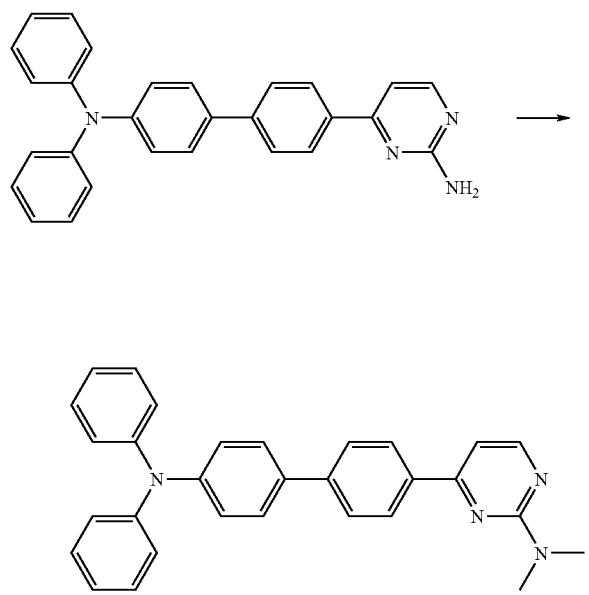

Sodium hydride (18 mg, 0.74 mmol) and 4-(4'-diphenylaminobiphenyl-4-yl)pyrimidine-2-amine (100 mg, 0.24 mmol) were added in anhydrous dimethylformamide (1 mL) for 30 minutes under nitrogen atmosphere. This solution was slowly added with a solution of iodomethane (86 mg, 0.6 mmol) in dimethylformamide (1 mL) for 30 minutes. This solution was stirred for 24 hours and added with water (100 mL) and a saturated saline solution. The precipitated crystalline material was purified by column chromatogram (silica gel, hexane:EtOAc=8:1) to obtain the title compound (60 mg).

Yield 57%: mp 140-141° C.; FTIR (KBr, v/cm$^{-1}$) 1582, 1558, 1490, 1402, 1280, 802, 752, 697; $^1$H-NMR (300 MHz, CDCl$_3$, ppm) δ 3.31 (s, 6H), 6.96 (d, J=5.1 Hz, 1H), 7.06 (t, J=7.3 Hz, 2H), 7.16 (d, J=8.1 Hz, 5H), 7.27-7.32 (m, 5H), 7.54 (d, J=8.4 Hz, 2H), 7.68 (d, J=8.0 Hz, 2H), 8.14 (d, J=8.0 Hz, 2H), 8.39 (d, J=5.1 Hz, 1H); $^{13}$C-NMR (75 MHz, CDCl$_3$, ppm) δ 37.19, 104.57, 123.16, 123.62, 124.62, 126.74, 127.50, 127.76, 128.89, 129.35, 134.00, 136.02, 142.71, 147.56, 147.69, 157.63, 163.97; UV λ$_{max}$=361 nm (CH$_2$Cl$_2$); PL λ$_{max}$=483 nm (CH$_2$Cl$_2$).

Example 8

Preparation of [4'-[2-(1,3-dihydroindole-2-yl)pyrimidine-4-yl]biphenyl-4-yl]diphenyl amine (compound 1-i)

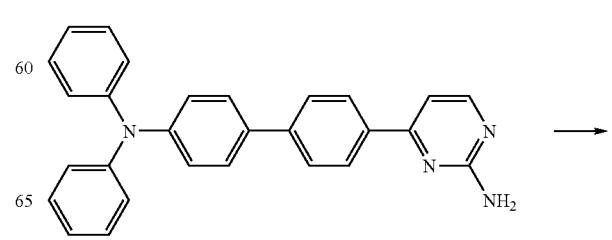

4-(4'-Diphenylaminobiphenyl-4-yl)pyrimidine-2-amine (100 mg, 0.24 mmol) and sodium hydroxide (38 mg, 0.96 mmol) were added in dimethylsulfoxide (1 mL), and stirred at 100° C. for 30 minutes. This solution was slowly added with a solution of 1,2-bis(bromomethyl)benzene (64 mg, 0.24 mmol) in dimethylsulfoxide (1 mL) for 30 minutes, and further stirred for 5 hours at 100° C. This solution was cooled and the precipitated solid was filtered and washed with dimethylsulfoxide and water, respectively, to obtain the title compound (97 mg).

Yield 79%; mp 247-248° C.; FTIR (KBr, v/cm$^{-1}$) 1579, 1561, 1505, 1490, 1461, 1339, 1283, 804, 752, 696; $^1$H-NMR (300 MHz, CDCl$_3$, ppm) δ 5.06 (s, 4H), 7.06-7.10 (m, 3H), 7.17 (d, J=7.7 Hz, 5H), 7.28-7.38 (m, 9H), 7.56 (d, J=8.4 Hz, 2H), 7.71 (d, J=8.0 Hz, 2H), 8.20 (d, J=8.1 Hz, 2H), 8.47 (d, J=5.2 Hz, 1H); $^{13}$C-NMR (75 MHz, CDCl$_3$, ppm) δ 52.99, 101.93, 105.38, 122.81, 123.16, 123.63, 124.64, 126.76, 127.26, 127.51, 127.77, 129.35, 134.04, 136.01, 137.72, 142.72, 147.58, 147.70, 158.34, 160.45, 164.03; UV λ$_{max}$=364 nm (CH$_2$Cl$_2$); PL λ$_{max}$=481 nm (CH$_2$Cl$_2$).

Example 9

Preparation of [4-(4'-diphenylaminobiphenyl-4-yl)pyrimidine-2-yl]phenylamine (compound 1-e)

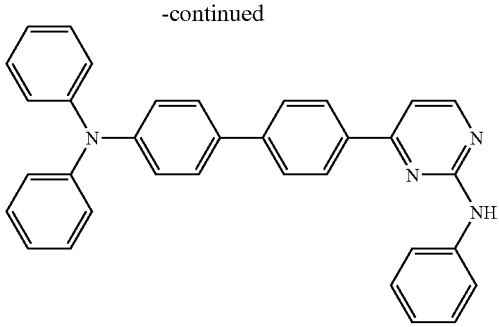

4-(4'-Diphenylaminobiphenyl-4-yl)pyrimidine-2-amine (100 mg, 0.24 mmol), bromobenzene (27.8 μL, 0.264 mmol), dichlorobis(triphenylphosphine)palladium(II) (17 mg, 0.024 mmol), Xantphos (14 mg, 0.024 mmol) and sodium t-butoxide (35 mg, 0.36 mmol) were added in toluene (3 mL), and fluxed under nitrogen atmosphere for 14 hours. This solution was cooled, and the precipitated solid was filtered and washed with cold toluene and water to obtain the title compound (98 mg).

Yield 83%; mp>300° C.; FTIR (KBr, v/cm$^{-1}$) 3290, 1583, 1494, 1438, 1281, 807, 749, 693; $^1$H-NMR (300 MHz, CDCl$_3$, ppm) δ 6.96-6.99 (m, 1H), 7.04-7.12 (m, 6H), 7.29-7.37 (m, 7H), 7.45 (d, J=5.7 Hz, 2H), 7.71 (d, J=8.7 Hz, 2H), 7.82-7.86 (m, 3H), 7.91 (d, J=7.4 Hz, 1H), 8.24 (d, J=8.2 Hz, 2H), 8.55 (d, J=5.0 Hz, 1 H), 9.67 (s, 1H); $^{13}$C-NMR (75 MHz, CDCl$_3$, ppm) δ 108.27, 119.27, 122.43, 123.19, 123.57, 124.66, 126.87, 127.56, 127.76, 128.94, 129.34, 133.78, 135.36, 139.71, 143.02, 147.55, 158.50, 160.30, 164.58.

Example 10

Preparation of [4-(4'-diphenylaminobiphenyl-4-yl)pyrimidine-2-yl]naphthalene-2-yl amine (compound 1-f)

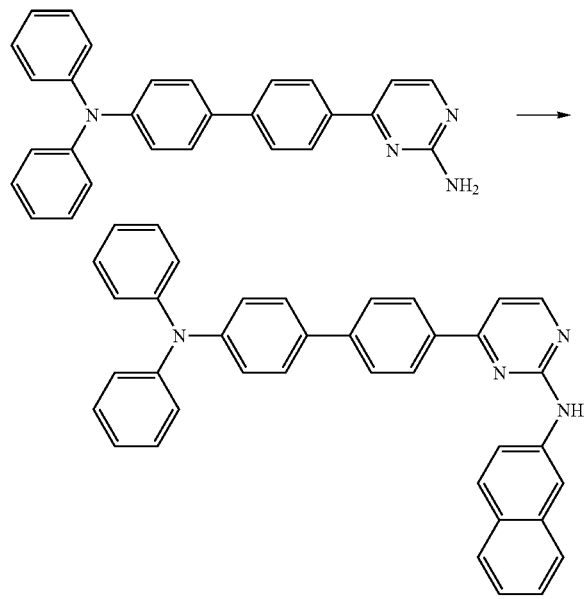

4-(4'-Diphenylaminobiphenyl-4-yl)pyrimidine-2-amine (100 mg, 0.24 mmol), 2-bromonaphthalene (54.6 mg, 0.264 mmol), dichlorobis(triphenylphosphine)palladium(II) (17 mg, 0.024 mmol), Xantphos (14 mg, 0.024 mmol) and sodium t-butoxide (35 mg, 0.36 mmol) were added in toluene (3 mL), and refluxed under nitrogen atmosphere for 14 hours. This solution was cooled, and the precipitated solid was washed with cold toluene and water to obtain the title compound (99 mg).

Yield 76%; mp>300° C.; FTIR (KBr, v/cm$^{-1}$) 3314, 1590, 1489, 1455, 1279, 807, 749, 693; $^1$H-NMR (300 MHz, CDCl$_3$, ppm) δ 7.06-7.12 (m, 7H), 7.32-7.58 (m, 7H), 7.72 (d, J=8.5 Hz, 2H), 7.81-7.92 (m, 7H), 8.30 (d, J=8.6 Hz, 2H), 8.61 (d, J=5.3 Hz, 2H), 9.92 (s, 1H); $^{13}$C-NMR (75 MHz, CDCl$_3$, ppm) δ 108.43, 114.89, 120.39, 123.19, 123.58, 124.17, 124.65, 126.34, 126.91, 127.35, 127.59, 127.79, 128.22, 128.57, 129.03, 129.34, 129.82, 133.76, 134.27, 137.20, 143.10, 147.54, 147.83, 158.55, 160.31, 164.60.

Example 11

Preparation of [4-(4'-diphenylaminobiphenyl-4-yl)pyrimidine-2-yl]biphenyl-4-yl amine (compound 1-g)

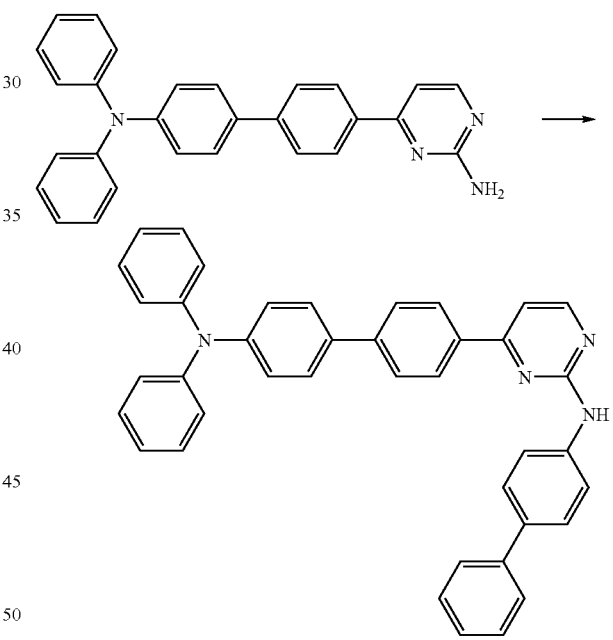

4-(4'-Diphenylaminobiphenyl-4-yl)pyrimidine-2-amine (100 mg, 0.24 mmol), 4-bromobiphenyl (61.5 mg, 0.264 mmol), dichlorobis(triphenylphosphine)palladium(II) (17 mg, 0.024 mmol), Xantphos (14 mg, 0.024 mmol) and sodium t-butoxide (35 mg, 0.36 mmol) were added in toluene (3 mL), refluxed under nitrogen atmosphere for 14 hours. This solution was cooled, and the precipitated solid was filtered and washed with cold toluene and water to obtain the title compound (125 mg).

Yield 92%; melting point>300° C.; FTIR (KBr, v/cm$^{-1}$) 3263, 1579, 1489, 1445, 1284, 803, 761, 750, 695; $^1$H-NMR (300 MHz, CDCl$_3$, ppm) δ 7.04-7.11 (m, 7H), 7.32-7.48 (m, 9H), 7.64-7.72 (m, 6H), 7.83 (d, J=8.3 Hz, 2H), 7.96 (d, J=8.7 Hz, 2H), 8.26 (d, J=8.4 Hz, 2H), 8.57 (d, J=5.2 Hz, 1H), 9.82 (s, 1H); $^{13}$C-NMR (75 MHz, CDCl$_3$, ppm) δ 108.38, 119.51, 123.21, 123.56, 124.67, 126.75, 126.90, 127.58, 127.77, 128.23, 128.75, 129.35, 133.75, 135.25, 139.06, 143.06, 147.55, 147.83, 158.54, 160.24.

Example 12

Preparation of [4-(4'-diphenylaminobiphenyl-4-yl)pyrimidine-2-yl]methylphenyl amine (compound 1-j)

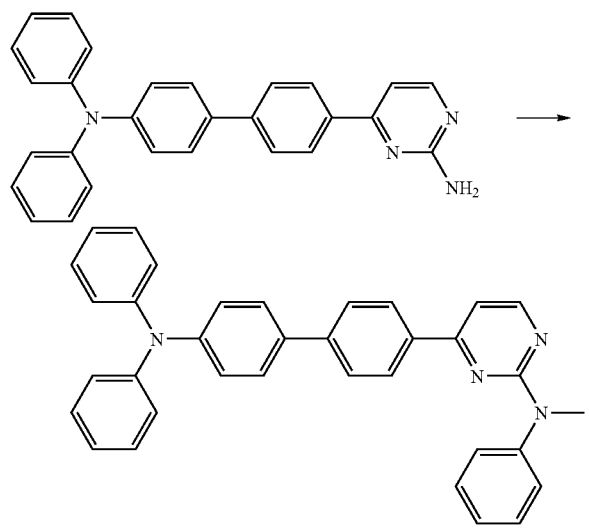

[4-(4'-Diphenylaminobiphenyl-4-yl)pyrimidine-2-yl]phenylamine (58.3 mg, 0.14 mmol) and sodium hydride (6 mg, 0.25 mmol) were slowly added in anhydrous dimethylformamide (1 mL) under nitrogen atmosphere for 30 minutes. This solution was added with a solution of iodomethane (30 mg, 0.21 mmol) in anhydrous dimethylformamide (1 mL) for 30 minutes, and stirred at room temperature for 24 hours. Upon completion of the reaction, the precipitated solid was filtered by column chromatogram (silica gel, hexane:EtOAc=8:1) to obtain the title compound (22 mg).

Yield 31%; mp 200-201° C.; FTIR (KBr, v/cm$^{-1}$) 1578, 1566, 1487, 1396, 1283, 807, 751, 694; $^1$H-NMR (300 MHz, CDCl$_3$, ppm) δ 3.68 (s, 3H) 7.05-7.11 (m, 3H), 7.16 (d, J=8.1 Hz, 5H), 7.27-7.33 (m, 6H), 7.43-7.48 (m, 4H), 7.53 (d, J=8.4 Hz, 2H), 7.67 (d, J=8.2 Hz, 2H), 8.10 (d, J=8.2 Hz, 2H), 8.41 (d, J=5.1 Hz, 1H); $^{13}$C-NMR (75 MHz, CDCl$_3$, ppm) δ38.82, 106.21, 123.19, 123.54, 124.66, 125.78, 126.49, 126.75, 127.59, 127.73, 129.06, 129.34, 133.79, 135.42, 143.04, 145.36, 147.54, 147.79; UV λ$_{max}$=362 nm (CH$_2$Cl$_2$); PL λ$_{max}$=488 nm (CH$_2$Cl$_2$).

Example 13

Preparation of [4-(4'-diphenylaminobiphenyl-4-yl)pyrimidine-2-yl]methyl naphthalene-2-ylamine (compound 1-k)

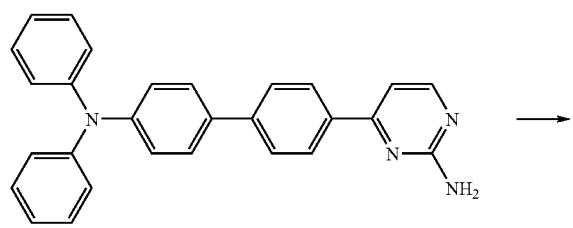

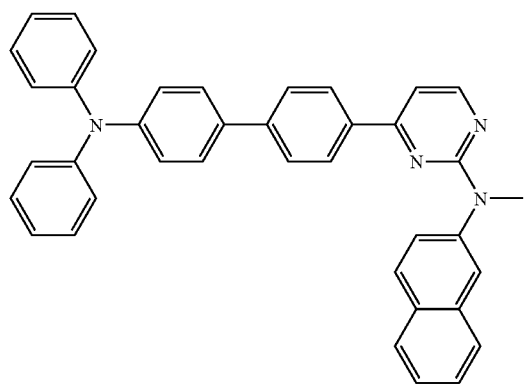

[4-(4'-Diphenylaminobiphenyl-4-yl)pyrimidine-2-yl]naphthalene-2-ylamine (58.3 mg, 0.14 mmol) and sodium hydride (6 mg, 0.25 mmol) were slowly added in anhydrous dimethylformamide (1 mL) under nitrogen atmosphere for 30 minutes. This solution was added with a solution of iodomethane (30 mg, 0.21 mmol) in anhydrous dimethylformamide (1 mL) for 30 minutes, and stirred at room temperature for 24 hours. Upon completion of the reaction, the precipitated solid was filtered by column chromatogram (silica gel, hexane:EtOAc=8:1) to obtain the title compound (36 mg).

Yield 46%; mp 204-205° C.; FTIR (KBr, v/cm$^{-1}$) 1577, 1565, 1489, 1397, 1282, 807, 750, 700; $^1$H-NMR (300 MHz, CDCl$_3$, ppm) δ 3.79 (s, 3H) 7.05-7.17 (m, 8H), 7.27-7.32 (m, 5H), 7.47-7.55 (m, 4H), 7.61-7.68 (m, 3H), 7.81-7.91 (m, 4H), 8.10 (d, J=8.1 Hz, 2H), 8.43 (d, J=5.2 Hz, 1H); $^{13}$C-NMR (75 MHz, CDCl$_3$, ppm) δ 38.80, 106.55, 123.11, 123.17, 123.60, 124.63, 125.45, 126.01, 126.19, 126.75, 127.49, 127.65, 127.74, 128.22, 129.45, 131.48, 133.92, 134.06, 142.79, 143.44, 147.57, 147.72, 158.17, 162.00, 163.75; UV λ$_{max}$=365 nm (CH$_2$Cl$_2$); PL λ$_{max}$=489 nm (CH$_2$Cl$_2$).

Example 14

Preparation of [4-(4'-diphenylaminobiphenyl-4-yl)pyrimidine-2-yl]methyl biphenyl-4-ylamine (compound 1-l)

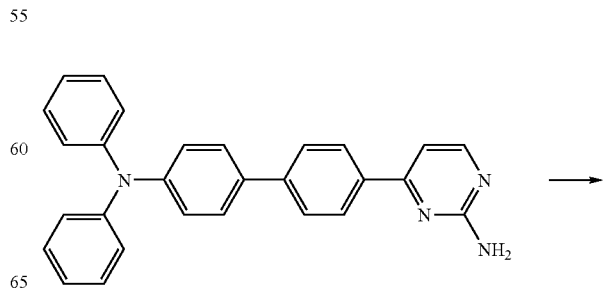

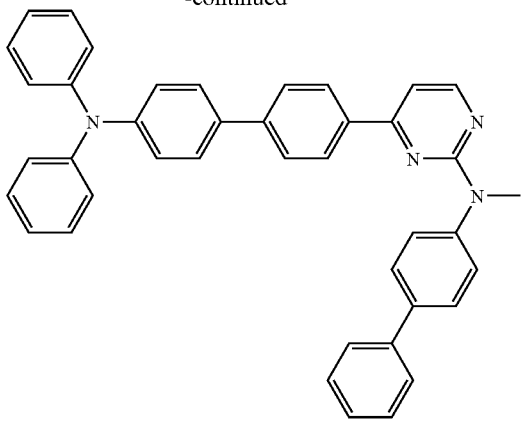

[4-(4'-Diphenylaminobiphenyl-4-yl)pyrimidine-2-yl]biphenyl-4-ylamine (58.3 mg, 0.14 mmol) and sodium hydride (6 mg, 0.25 mmol) were slowly added in anhydrous dimethylformamide (1 mL) under nitrogen atmosphere for 30 minutes. This solution was added with a solution of iodomethane (30 mg, 0.21 mmol) in anhydrous dimethylformamide (1 mL) for 30 minutes, and stirred at room temperature for 24 hours. Upon completion of the reaction, the precipitated solid was filtered by column chromatogram (silica gel, hexane: EtOAc=8:1) to obtain the title compound (48 mg).

Yield 59%; mp 224-225° C.; FTIR (KBr, v/cm$^{-1}$) 1584, 1560, 1490, 1395, 1271, 809, 753, 694; $^{1}$H-NMR (300 MHz, CDCl$_3$, ppm) δ 3.73 (s, 3H) 7.05-7.18 (m, 9H), 7.28-7.39 (m, 6H), 7.45-7.56 (m, 6H), 7.67-7.70 (m, 5H), 8.13 (d, J=7.9 Hz, 2H), 8.43 (d, J=4.9 Hz, 1H); $^{13}$C-NMR (75 MHz, CDCl$_3$, ppm) δ 38.57, 106.47, 123.16, 123.61, 124.63, 126.53, 126.76, 127.06, 127.12, 127.48, 127.58, 127.74, 128.77, 129.33, 133.95, 135.76, 138.12, 140.83, 142.77, 144.94, 147.57, 147.72, 158.26, 162.00, 163.76; UV λ$_{max}$=365 nm (CH$_2$Cl$_2$); PL λ$_{max}$=486 nm (CH$_2$Cl$_2$).

Test Example

Analysis of UV and Photo-Luminescent Properties

UV-spectra and photo-spectra of the compounds of Formula 1 according to the present invention were measured with a UV/Visible spectrometer (S-2130 spectroscopy) and a luminescent spectroscopy ((PL, JRF-5301-PC), respectively, at the concentrations of 50 μM and 100 nM by using dichloromethane as a solvent. The results are presented in Table 1. For ascertaining solvatochromism, photo-luminescent properties were also investigated by using various organic solvents, and the results are provided in Table 2.

TABLE 1

| Compound No. | λ$_{max}$ (nm) UV[a] | λ$_{max}$ (nm) PL[b] | FWHM[c] (nm) |
|---|---|---|---|
| 4 | 365 | 500 | 82 |
| 5 | 363 | 493 | 91 |
| 1-a | 366 | 497 | 80 |
| 1-b | 365 | 483 | 75 |
| 1-c | 363 | 479 | 76 |
| 1-d | 365 | 479 | 76 |
| 1-h | 361 | 483 | 75 |
| 1-i | 364 | 481 | 80 |
| 1-j | 362 | 488 | 78 |
| 1-k | 365 | 489 | 104 |
| 1-l | 365 | 486 | 102 |

[a] UV measured in CH$_2$Cl$_2$ solution at 50 μM
[b] PL recorded by single beam excitation in CH$_2$Cl$_2$ solution at 100 nM concentration
[c] The full widths at half maximum value

TABLE 2

| Solvent | λ$_{max}$ (nm)[a] 1-i | λ$_{max}$ (nm)[a] 1-b | RI[b] (%) 1-i | RI[b] (%) 1-b |
|---|---|---|---|---|
| Toluene | 438 | 437 | 127 | 119 |
| Diethylether | 454 | 451 | 85.3 | 32.4 |
| THF | 470 | 465 | 68.3 | 106 |
| Dichloromethane | 481 | 483 | 100 | 100 |
| DMF | 502 | 506 | 37.5 | 62.8 |
| DMSO | 510 | 506 | 52 | 61 |

[a] All readings were made at 100 nM concentration
[b] RI = Relative intensity of PL as a percent of PL in CH$_2$Cl$_2$ As described above, diphenyl amine derivatives of the present invention are useful for blue and blue-green fluorescent dye, and can also be used as luminescence material for the manufacture of all kinds of display comprising organic electroluminescence display or luminescence substance such as a flat panel display.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:
1. Diphenyl amine derivatives of Formula 1:

Formula 1

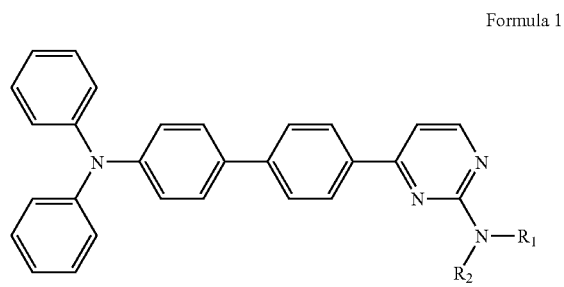

wherein each of R$_1$ and R$_2$ is selected from the group consisting of a hydrogen atom; a C$_1$-C$_8$ alkyl; a substituted or unsubstituted phenyl; a biphenyl; a substituted or unsubstituted naphthyl; and a substituted or unsubstituted benzyl group, wherein the substituted benzyl group is substituted with a C$_1$-C$_8$ alkyl or a C$_1$-C$_8$ alkoxy group; and each of the substituted phenyl and the substituted naphthyl groups are substituted with 1-3 substituent(s) selected from the group consisting of a halogen atom, cyano, nitro, carboxyl, sulfonyl, hydroxy, amino, a C$_1$-C$_8$ alkylamino, a C$_1$-C$_8$ alkyl, a C$_1$-C$_8$ alkoxy, a C$_2$-C$_8$ alkenyl, phenyl, 4-styryl, phenoxy, naphthoxy, phenylamino, and naphthylamino groups.

2. The diphenyl amine derivatives of claim 1, wherein each of $R_1$ and $R_2$ is selected from the group consisting of a hydrogen atom; an alkyl selected from the group consisting of methyl, ethyl, n-propyl, isopropyl, n-butyl, sec-butyl and tert-butyl groups; phenyl; biphenyl; naphthyl; and a substituted or unsubstituted benzyl group, wherein the substituted benzyl group is substituted with substituent(s) selected from the group consisting of methyl, ethyl, n-propyl, isopropyl, n-butyl, sec-butyl, tert-butyl, methoxy, ethoxy, n-propoxy, isopropoxy, n-butoxy, sec-butoxy, and tert-butoxy groups.

3. The diphenyl amine derivatives of claim 1, which is selected from the group consisting of the following compounds:

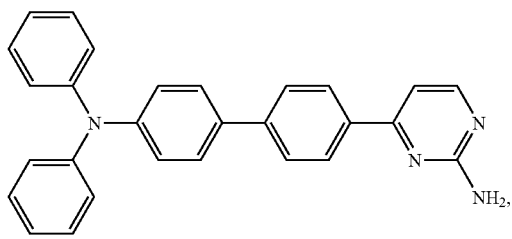

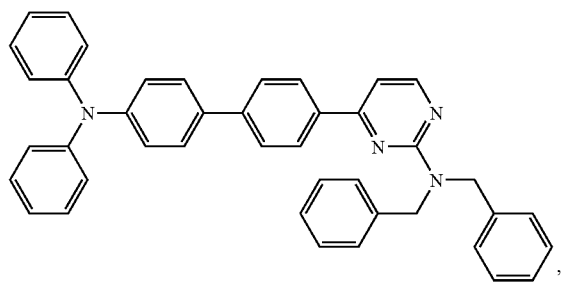

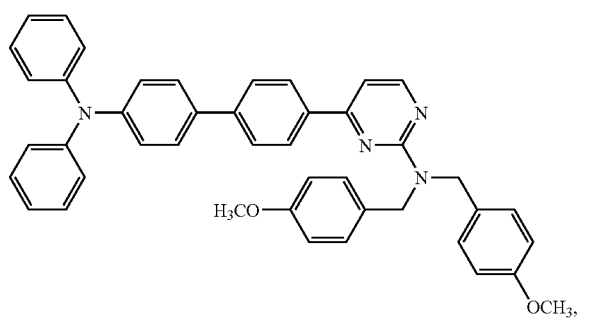

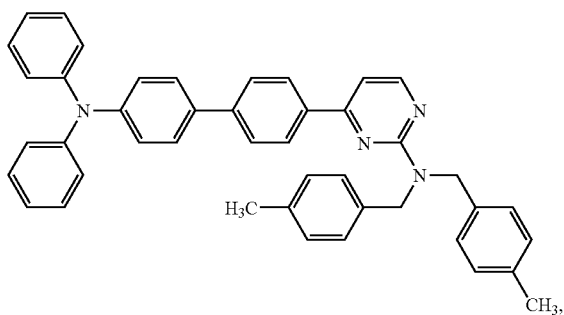

-continued

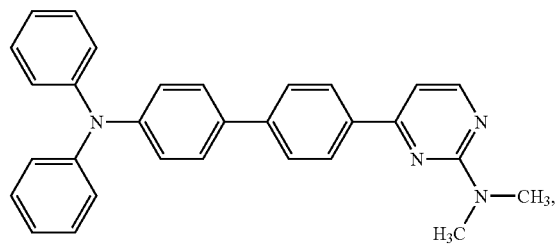

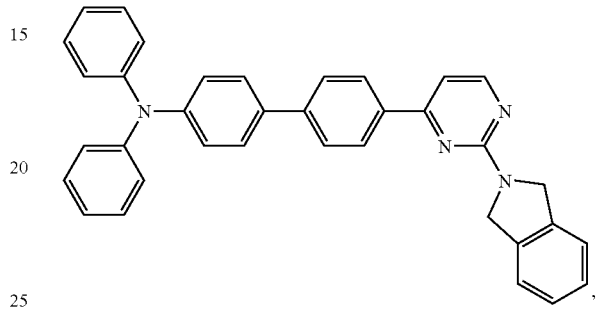

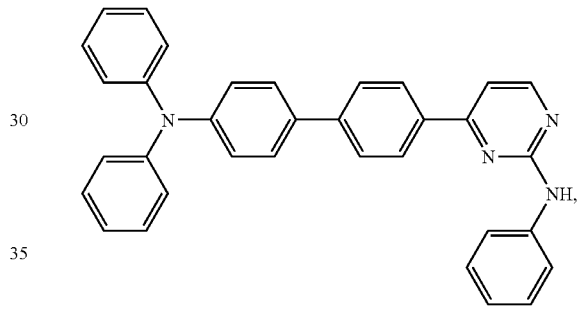

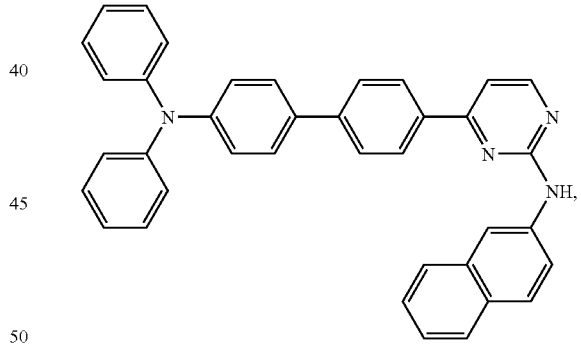

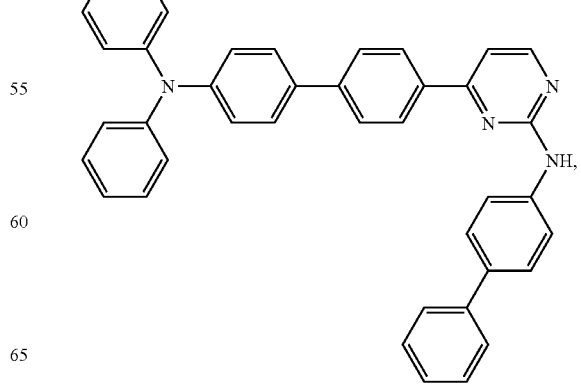

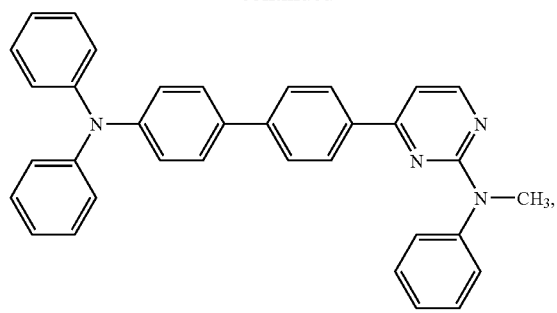

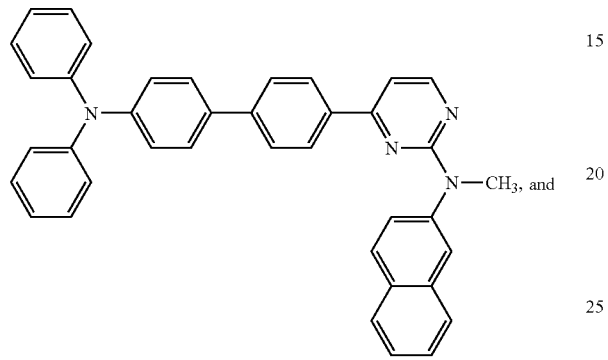

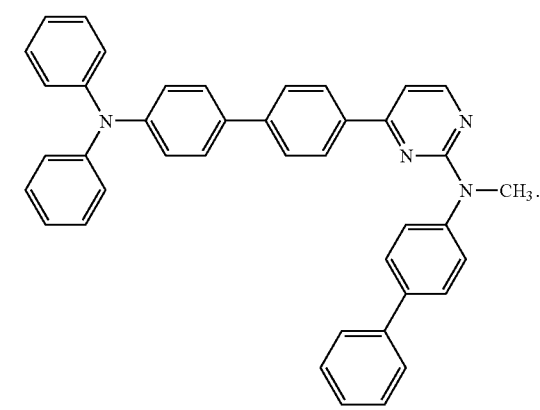

4. A process of preparing diphenyl amine derivatives comprising the steps of:

A. preparing an ethanone compound of Formula 4 by reacting a bromide compound of Formula 2 with a borate compound of Formula 3 in the presence of palladium (Pd) catalyst and under nitrogen atmosphere;

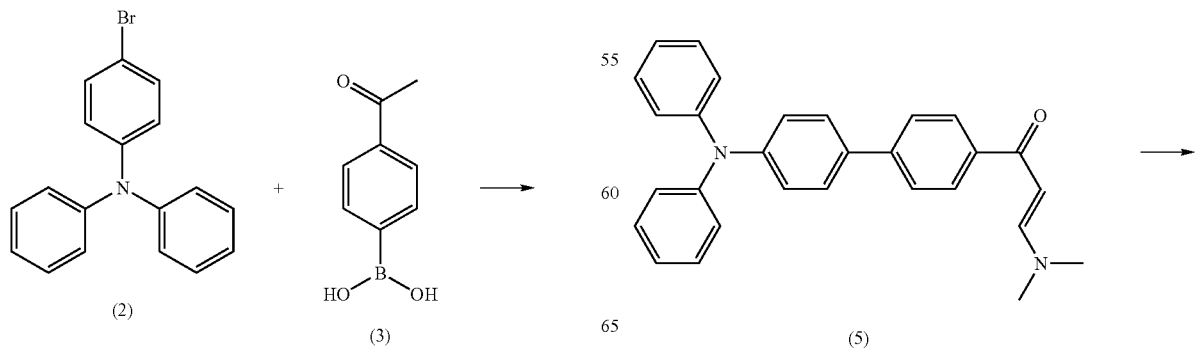

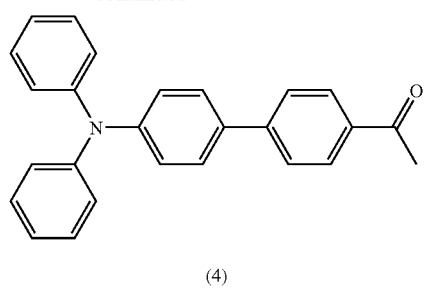

B. preparing a propenone compound of Formula 5 by reacting the ethanone compound of Formula 4 with N,N-dimethylformamide dimethylacetal;

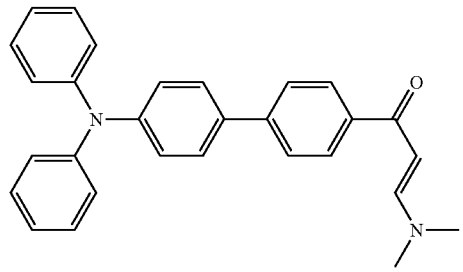

C. preparing an amine compound of Formula 1a by reacting the propenone compound of Formula 5 with sodium ethoxide and guanidine hydrochloride; and -continued
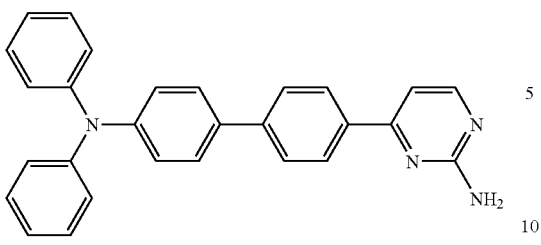
(1a)
D. preparing the diphenyl amine derivatives of Formula 1 by reacting the amine compound of Formula 1a with a halide compound of $R_1$—X or $R_2$—X;
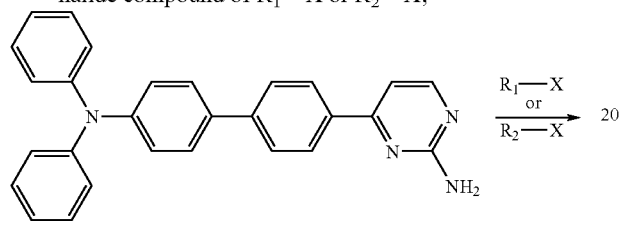
(1a)
-continued
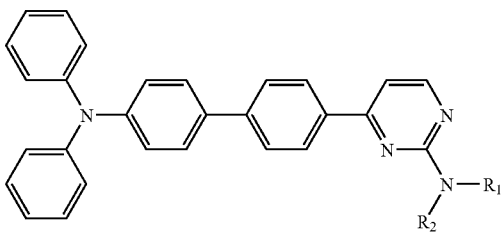
(1)
wherein X is a halogen atom; each of $R_1$ and $R_2$ is same as defined in claim 1 with a proviso either of $R_1$ and $R_2$ is not hydrogen.
* * * * *